United States Patent [19]

Kaneko et al.

[11] Patent Number: 4,601,829

[45] Date of Patent: Jul. 22, 1986

[54] PURIFICATION OF LYSINE BY REVERSE-PHASE OSMOSIS

[75] Inventors: Tetsuya Kaneko, Kawasaki; Masaru Saeki, Fujisawa; Kiyoshi Tanaka, Tokyo; Tetsuya Kawakita, Yokohama, all of Japan

[73] Assignee: Ajinomoto Co., Inc., Tokyo, Japan

[21] Appl. No.: 685,792

[22] Filed: Dec. 24, 1984

[30] Foreign Application Priority Data

Dec. 27, 1983 [JP] Japan ................................ 58-248947

[51] Int. Cl.$^4$ ............................................. B01D 13/00
[52] U.S. Cl. .................................... 210/638; 210/652; 210/663; 210/677; 426/656; 562/514
[58] Field of Search ............... 210/638, 652, 663, 677; 426/656; 562/514

[56] References Cited

U.S. PATENT DOCUMENTS 3,565,951  2/1971  Ishida et al. .......................... 562/514
3,962,077  6/1976  Pascarella et al. ................... 210/638
4,440,795  4/1984  Goldstein et al. .............. 426/495 X

OTHER PUBLICATIONS

Chem. Abst., vol. 92, No. 21, May 26, 1980, p. 495, Ref. No. 179292w, Lawhon et al.: "An Improved Process for Isolation of Glandless Cottonseed Protein Using Industrial Membrane Systems", J. Food Sci. 1980.
Chem. Abst., vol. 86, No. 21, May 23, 1977, p. 340, Ref. No. 153979b, US; & JP-A-77 01 092 (Ajinomoto Co., Inc.) 1/6/77.
Porter, M. C. et al., "Membrane Ultrafiltration", Chem. Tech., Jan. 1971, pp. 56–63.
Perry, Robert H., et al, *Chemical Engineers' Handbook*, Fifth Edition, McGraw-Hill Book Co., N.Y., 1973, pp. 17-40 to 17-43.

*Primary Examiner*—David Sadowski
*Attorney, Agent, or Firm*—Oblon, Fisher, Spivak, McClelland & Maier

[57] ABSTRACT

A process for purifying lysine in a lysine production process, which involves passing a solution containing lysine over a cation exchange resin such that lysine adsorbs onto the resin, eluting adsorbed lysine from the resin with an aqueous solution of ammonia to produce a lysine-containing elution liquid, passing the elution liquid directly to a reverse osmosis membrane system, and concentrating the lysine-containing elution liquid with the reverse osmosis membrane system such that ammonia is selectively removed from the lysine containing elution; the aqueous ammonia which is separated from the lysine may be recycled through the cation exchange resin to regenerate the resin or to elute more lysine from the resin.

5 Claims, No Drawings

PURIFICATION OF LYSINE BY REVERSE-PHASE OSMOSIS

BACKGROUND OF THE INVENTION

1. Field of the Invention

The present invention relates to a separation and recovery process of lysine by concentrating a lysine-containing elution liquid with a reverse osmosis membrane, which elution liquid has been eluted from a lysine-adsorbing cation exchange resin with ammonia water. The present invention relates also to a lysine production process in which ammonia permeated through a reverse osmosis membrane with water is recovered and recycled as a resin elution agent or a regeneration agent for the next cycle of the resin treatment.

2. Description of the Related Art

Lysine is one of the most important amino acids as a cattle feed additive and is produced mainly by the fermentation method.

As to the treatment process of a lysine fermentation liquid, the method with the use of a strongly acidic cation exchange resin has been generally applied. This method, for example, is to elute lysine with the use of a low-priced elution agent such as ammonia water, after adsorbing lysine by contacting a lysine fermentation liquid conditioned to a certain pH, with a salt-type cation exchange resin such as ammonium-type one.

As a method to recover lysine from a resin elution liquid, a known method is to crystallize and separate a lysine mineral acid salt (lysine hydrochloric acid salt, lysine sulfuric acid salt, for example) by neutralization with addition of an acid, after concentration under a reduced pressure at an elevated temperature. In this method, it was possible to recycle, the dilute ammonia water obtained through condensation of ammonia-containing vapor as a part of elution agent of the cation exchange resin. In this method, however, there was a weak point that a great amount of heat energy is needed, such as latent heat necessary for evaporation, other than sensible heat. Furthermore, it was inevitable that lysine reacted with other impurities by the heat, which resulted in quality deterioration and yield reduction, such as browning of a liquid and decomposition of lysine.

On the other hand, from the viewpoint of environmental preservation, ammonia vapor produced is harmful and recovery by a cooling system is not perfect. To prevent its discharge into the air, measures are taken, for example, by absorbing with acid liquid or catching with current water. A great amount of cost had been needed to observe the nitrogen content regulation and pH regulation specified for discharged water.

SUMMARY OF THE INVENTION

The object of the present invention is to provide a novel method to produce lysine at a high yield with a small amount of energy and with easy environmental preservation, in a process of recovering lysine by concentration from a lysine-containing resin elution liquid.

As a result of various researches to attain the said object, the inventors have achieved the present invention by finding that it is possible to perform concentration, with low energy and with high efficiency, of a lysine-containing liquid with a reverse osmosis membrane, and further to recycle, as resin regeneration agent or elution agent, a permeated ammonia water.

That is to say, in the method in which lysine is recovered from a lysine fermentation liquid by resin treatment, for example, the present invention is a lysine production process characterized by concentrating, with a reverse osmosis membrane, a lysine-containing liquid in which ammonia water is used as resin elution agent, and by recovering and recycling ammonia permeated through the membrane with water.

DESCRIPTION OF THE PREFERRED EMBODIMENTS

The fermentation liquid means hereunder is not only a fermented broth of L-lysine fermented with a microorganism in a medium using, as carbon source, for example, beet molasses, cane molasses, starch, glucose or mixture thereof, but also a formed reaction liquid of L- and/or D-lysine reacted with an enzyme or microorganism.

In the process of the present invention, it goes without saying that lysine adsorbed to a cation exchange resin cannot be limited to one originating from the above-mentioned fermentation method, but may be one originating from a synthesis method. Lysine can be adsorbed to a cation exchange resin by either method, and there is no limitation as to cation exchange resin. Elution of lysine with ammonia water from a lysine-adsorbing cation exchange resin can be achieved by an appropriate method. Ammonia water can be added with an ammonium salt such as ammonium chloride, ammonium sulfate, etc, as an additional agent. Any of these is self-evident to those skilled in the art.

As a reverse osmosis membrane, one put into practical use domestically or abroad can be used, but necessarily with resistance to alkali. As its materials, for example, there are polyether/amide, polyacrylonitrile, polybenzoimidazolone, aromatic amide, etc. As to the type of reverse osmosis membranes, flat membrane type, tubular type, spiral type, hollow fiber type, etc. are commercialized, and either of the types can be used. As to the performance of a membrane, membranes of NaCl inhibition rate of more than 90%, preferably more than 95% are used.

As to the treatment pressure and temperature in reverse osmosis concentration, they are preferably as high as possible, within the limitation range of the membrane quality and module structure, but there is no other particular limitation thereof. It is conducted normally at pressure of 20–60 kg/cm$^2$ and temperature of 30°–60° C. Concentration can be conducted up to a point where a concentration rate is decided by the osmotic pressure of an object liquid, quality of a membrane and limit pressure of a module structure; in accordance with the necessity, it is possible to easily obtain a concentration rate appropriate for crystallization of lysine, if an additional small concentration is made under reduced pressure. Water or ammonia permeated through membrane can be used as a regeneration, or eluting agent of a resin, by recycling again to a resin process, as it is or, if necessary, after adjusting the concentration through addition of liquid ammonia. There has been so far no example in which a matter permeating through a reverse osmosis membrane with water is used, as in the present invention.

The recovery of lysine from the concentrate by reverse osmosis can be made by a common method; for example, by addition of a mineral acid such as chloric acid, and concentration or cooling crystallization. Then lysine can be recovered as a lysine mineral acid salt satisfactory for feed.

Further explanation is given in the following examples.

EXAMPLE 1

A lysine fermentation liquid obtained by using beet molasses as a carbon source and ammonium sulfate as nitrogen source, was added with 98% sulfuric acid to pH2, and was passed through a strong-cation exchange resin (SK-1B, $NH_4^+$ type, Mitsubishi Chemical Industries, Ltd.).

A resin elution liquid of 300 ml was obtained through elution of 3.4% ammonia water after adsorption. At this time, the concentration of lysine was 7.0% (w/w), concentration of ammonia was 1.8% (w/w) and pH was 10.0.

This elution liquid was concentrated at temperature of 40° C. and at pressure of 40 kg/cm$^2$ for 25 hours, with a reverse osmosis system equipped with a reverse osmosis membrane made by Teijin, Ltd., PBIL TL-198 (flat type, 0.0025 m$^2$, made of polybenzimidazolone).

When the concentration rate registered 3.1 times, a concentrate of 95 ml and a permeated liquid of 201 ml were taken out and analyzed with the results shown in Table 1.

TABLE 1

|  | Lysine Concentration % (w/w) | Ammonia Concentration % (w/w) | pH |
|---|---|---|---|
| Permeated liquid | 0.2 | 0.2 | 10.5 |
| Concentrate | 21.6 | 5.2 | 9.9 |

That is to say, the inhibition rate of ammonia was 92%, inhibition rate of lysine was 98% and the other cations ($K^+$, $Na^+$, $Ca^{++}$, $Mg^{++}$) were inhibited by 99% or more.

This permeated liquid was added with liquid ammonia to prepare again 3.4% ammonia water; through resin adsorption and elution by the same method as mentioned before, a resin elution liquid of 300 ml was obtained. At this time, the concentration of lysine was 7.1% (w/w), concentration of ammonia was 1.8% (w/w), and pH was 10.1.

This elution liquid was submitted to reverse osmosis concentration on the same condition as that mentioned before; when the concentration rate was increased to 3.0 times for 24-hour concentration, a concentrate of 98 ml and a permeated liquid of 199 ml were taken out and analyzed with the results shown in Table 2.

TABLE 2

|  | Lysine Concentration % (w/w) | Ammonia Concentration (% w/w) | pH |
|---|---|---|---|
| Permeated liquid | 0.2 | 0.2 | 10.6 |
| Concentrate | 21.1 | 5.0 | 9.8 |

That is to say, the inhibition rate of ammonia was 91%, the inhibition of lysine was 98%, and the other cations ($K^+$, $Na^+$, $Ca^{++}$, $Mg^{++}$) were inhibited by 99% or more.

Energy consumed during a series of the tests was only for heat preservation of a liquid, circulation of a liquid and pressurization, contributing much to reduction of energy consumption; in addition to this merit, it was possible to completely prevent formation of ammonia vapor and discharge of ammonia-containing water which had occurred so far in an evaporation process.

EXAMPLES 2

By the use of a lysine fermentation liquid obtained according to the same method as that mentioned in Example 1, an adsorption was conducted in the same manner, and an adsorbed lysine was eluted with a liquid mixture of 3.4% ammonia water and 10.5% ammonium chloride at the rate of 1:1 (v/v), thus obtaining a resin elution liquid of 300 ml. At this time, the concentration of lysine was 6.3% (w/w), concentration of ammonia was 1.7% (w/w) and pH was 9.5.

This elution liquid was concentrated for 25 hours at temperature of 40° C. and at pressure of 40 kg/cm$^2$, by the use of a reverse osmosis system equipped with a reverse osmosis membrane made by Denmark Sugar-Manufacturing Co. (DDS), HR-95 (flat membrane-type, 0.0025 m$^2$).

When the concentration rate was increased up to 3.5 times, a concentrate of 85 ml and permeated liquid of 213 ml were taken out and analyzed with the results given in Table 3.

TABLE 3

|  | Lysine Concentration % (w/w) | Ammonia Concentration % (w/w) | pH |
|---|---|---|---|
| Permeated liquid | 0.4 | 0.5 | 10.1 |
| Concentrate | 21.1 | 4.7 | 9.3 |

That is to say, the inhibition rate of ammonia was 79%, inhibition rate of lysine was 95% and the other cations ($K^+$, $Na^+$, $Ca^{++}$, $Mg^{++}$) were inhibited by 99% or more.

What is claimed is:

1. A process of purifying lysine including separating lysine from aqueous ammonia, which comprises:
   passing a solution containing lysine over a cation exchange resin such that lysine adsorbs onto said resin,
   eluting adsorbed lysine from said resin with an aqueous solution of ammonia, to produce a lysine-containing elution liquid,
   passing said lysine-containing elution liquid directly to a reverse osmosis membrane system, and
   concentrating the lysine-containing elution liquid with said reverse osmosis membrane system, wherein said concentrating allows selective removal of ammonia relative to lysine from said lysine-containing elution liquid in the absence of electrolysis, and wherein said concentrating step is conducted under a pressure of 20–60 kg/cm$^2$ and a temperature of 30°–60° C.

2. The process of claim 1, which further comprises:
   recycling an aqueous solution containing ammonia which has permeated through a reverse osmosis membrane in said reverse osmosis membrane system, through a cation exchange resin, wherein said recycling is carried out in order to regenerate said resin or to elute more lysine from said resin.

3. The process of claim 1, wherein ammonia in said aqueous solution is derived from an ammonium salt.

4. The process of claim 1, wherein said reverse osmosis membrane system contains a reverse osmosis membrane which has a sodium chloride inhibition rate of more than 90%.

5. The process of claim 4, wherein said rate is more than 95%.

* * * * *